United States Patent
Polak (10) Patent No.: US 10,721,574 B2
(45) Date of Patent: Jul. 21, 2020

(54) FITTING UNILATERAL ELECTRIC ACOUSTIC STIMULATION FOR BINAURAL HEARING

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/816,173

(22) Filed: Aug. 3, 2015

(65) Prior Publication Data

US 2015/0341731 A1 Nov. 26, 2015

Related U.S. Application Data

(63) Continuation-in-part of application No. PCT/US2014/014648, filed on Feb. 4, 2014, and a
(Continued)

(51) Int. Cl.
*A61N 1/05* (2006.01)
*H04R 25/00* (2006.01)
(Continued)

(52) U.S. Cl.
CPC ........... *H04R 25/70* (2013.01); *A61B 5/4851* (2013.01); *A61N 1/0541* (2013.01);
(Continued)

(58) Field of Classification Search
CPC ... A61N 1/0541; A61N 1/36063; A61F 11/04; H04R 25/353
See application file for complete search history.

(56) References Cited

U.S. PATENT DOCUMENTS 8,086,319 B2 * 12/2011 van Dijk ............ A61N 1/36032
600/379
8,244,365 B2 * 8/2012 Dijk .................... A61N 1/36032
600/559
(Continued)

FOREIGN PATENT DOCUMENTS

WO WO 92/08330 A1 5/1992 ............. H04R 25/00
WO WO 14/123890 A1 8/2014 ............... A61N 1/36

OTHER PUBLICATIONS

Gantz et al., "Combining Acoustic and Electrical Speech Processing: Iowa/Nucleus Hybrid Implant," Acta Otolaryngol, vol. 124, pp. 344-347, 2004.
(Continued)

*Primary Examiner* — Tammie K Marlen
(74) *Attorney, Agent, or Firm* — Sunstein LLP (57) ABSTRACT

A system and method of fitting an Electric Acoustic Stimulation (EAS) system of a patient that has binaural hearing is provided. The patient has an ipsilateral ear and a contralateral ear opposite the ipsilateral ear, with the EAS system associated with the ipsilateral ear of the patient. Stimulation parameters of the EAS system are developed unilaterally while taking into account hearing abilities of the contralateral ear. The EAS system is configured based on the developed stimulation parameters.

16 Claims, 4 Drawing Sheets

Related U.S. Application Data continuation-in-part of application No. 13/667,142, filed on Nov. 2, 2012, now Pat. No. 9,113,270.

(60) Provisional application No. 61/761,063, filed on Feb. 5, 2013, provisional application No. 61/557,456, filed on Nov. 9, 2011, provisional application No. 61/555,599, filed on Nov. 4, 2011.

(51) Int. Cl.
*A61B 5/00* (2006.01)
*A61N 1/36* (2006.01)
*A61B 5/12* (2006.01)

(52) U.S. Cl.
CPC .......... *A61N 1/36036* (2017.08); *A61B 5/125* (2013.01); *H04R 25/353* (2013.01)

(56) References Cited

U.S. PATENT DOCUMENTS

| | | |
|---|---|---|
| 8,295,497 B2 | 10/2012 | Roeck et al. ................. 381/23.1 |
| 9,113,270 B2 | 8/2015 | Polak ............................. 607/55 |
| 9,440,071 B2 * | 9/2016 | Mishra ............... A61N 1/36032 |
| 2004/0172101 A1 | 9/2004 | Van Hoesel ..................... 607/57 |
| 2006/0287690 A1 | 12/2006 | Bouchataoui et al. ......... 607/57 |
| 2008/0123886 A1 | 5/2008 | Andersen et al. ............ 381/320 |
| 2009/0264961 A1 | 10/2009 | Schleich et al. ................ 607/57 |
| 2009/0264963 A1 | 10/2009 | Faltys et al. .................... 607/57 |
| 2010/0198300 A1 | 8/2010 | Smith ............................. 607/57 |
| 2010/0280307 A1 | 11/2010 | Lineaweaver et al. ......... 600/25 |
| 2011/0249843 A1 | 10/2011 | Holmberg et al. ........... 381/316 |
| 2012/0224705 A1 | 9/2012 | Meskens et al. ............ 381/23.1 |
| 2013/0004000 A1 | 1/2013 | Franck .......................... 381/314 |
| 2013/0051566 A1 * | 2/2013 | Pontoppidan ........ H04R 25/353 381/23.1 |

OTHER PUBLICATIONS

Greenwood, "A Cochlear Frequency-Position Function for Several Species—29 years later," J. Acoust. Soc. Am., vol. 87, No. 6, pp. 2592-2605, Jun. 1990.

Gstoettner et al., Hearing Preservation in Cochlear Implantation for Electric Acoustic Stimulation, Acta Otolaryngol, vol. 124, pp. 348-352, 2004.

Nopp et al., "From Electric Acoustic Stimulation to Improved Sound Coding in Cochlear Implants," Van de Heyning P, Kleine Punte A (eds): Cochlear Implants and Hearing Preservation, Advances in Oto-Rhino-Laryngology, vol. 67, pp. 88-95, 2010.

Polak et al., "Fitting of the Hearing System Affects Partial Deafness Cochlear Implant Performance," Cochlear Implants International, vol. 11, Supplement 1, pp. 117-121, Jun. 2010.

Skarzynski et al., "Preservation of low frequency hearing in partial deafness cochlear implantation (PDCI) using the round window surgical approach," Acta Oto-Laryngologica, vol. 127, pp. 41-48, 2007.

Von Ilberg et al., "Electric-Acoustic Stimulation of the Auditory System," ORL, vol. 61, pp. 334-340, 1999.

United States Patent and Trademark Office, Office Action dated Jan. 15, 2015 pertaining to U.S. Appl. No. 13/667,142, 11 pages.

United States Patent and Trademark Office, Notice of Allowance and Fee(s) Due dated May 8, 2015 pertaining to U.S. Appl. No. 13/667,142, 5 pages.

International Searching Authority, International Search Report—International Application No. PCT/US14/14648, dated Apr. 29, 2014, together with the Written Opinion of the International Searching Authority, 17 pages.

Ching et al., "Binaural-Bimodal Fitting or Bilateral Implantation for Managing Severe to Profound Deafness: A Review," Trends in Amplification, vol. 11, No. 3, Sep. 2007, pp. 161-192.

European Patent Office, Extended European Search Report—Application No. 14749385.2-1910 dated Aug. 24, 2016, 9 pages.

\* cited by examiner

A - USABLE A HEARING

E - E HEARING ACCORDING TO THE GREENWOOD SCALE

E' - MODIFIED E HEARING BY STIMULATING LOWER FREQUECIES THAN THE GREENWOOD SCALE SUGGESTS

FIG. 4b

A - USABLE A HEARING

E - E HEARING ACCORDING TO THE GREENWOOD SCALE

E' - MODIFIED E HEARING BY TURNING OFF APICAL CHANNELS

# FITTING UNILATERAL ELECTRIC ACOUSTIC STIMULATION FOR BINAURAL HEARING

CROSS-REFERENCE TO RELATED APPLICATIONS

This application is a continuation-in-part of Patent Cooperation Treaty Application PCT/US2014/014648, filed Feb. 4, 2014, entitled "Fitting Unilateral Electric Acoustic Stimulation for Binaural Hearing," which in turn claims priority from U.S. provisional patent application Ser. No. 61/761,063, filed Feb. 5, 2013, entitled "Unilateral Fitting Process In Electric Acoustic Stimulation In Patients With Binaural Hearing."

This application is also a continuation-in-part of U.S. patent application Ser. No. 13/667,142, filed Nov. 2, 2012, entitled "Transpositional Acoustic Frequency Range In EAS Patients," now U.S. Pat. No. 9,113,270, which in turn claims priority from U.S. provisional patent application 61/555,599 filed Nov. 4, 2011, entitled "Transpositional Acoustic Frequency Range In EAS Patients," and U.S. provisional patent application 61/557,456 filed Nov. 9, 2011, entitled "Transpositional Acoustic Frequency Range In EAS Patients."

All of the aforementioned patent applications are hereby incorporated by reference in their entirety.

TECHNICAL FIELD

The present invention relates to systems and methods for fitting an Electric Acoustic Stimulation (EAS) system of a patient.

BACKGROUND ART

Figure 1:
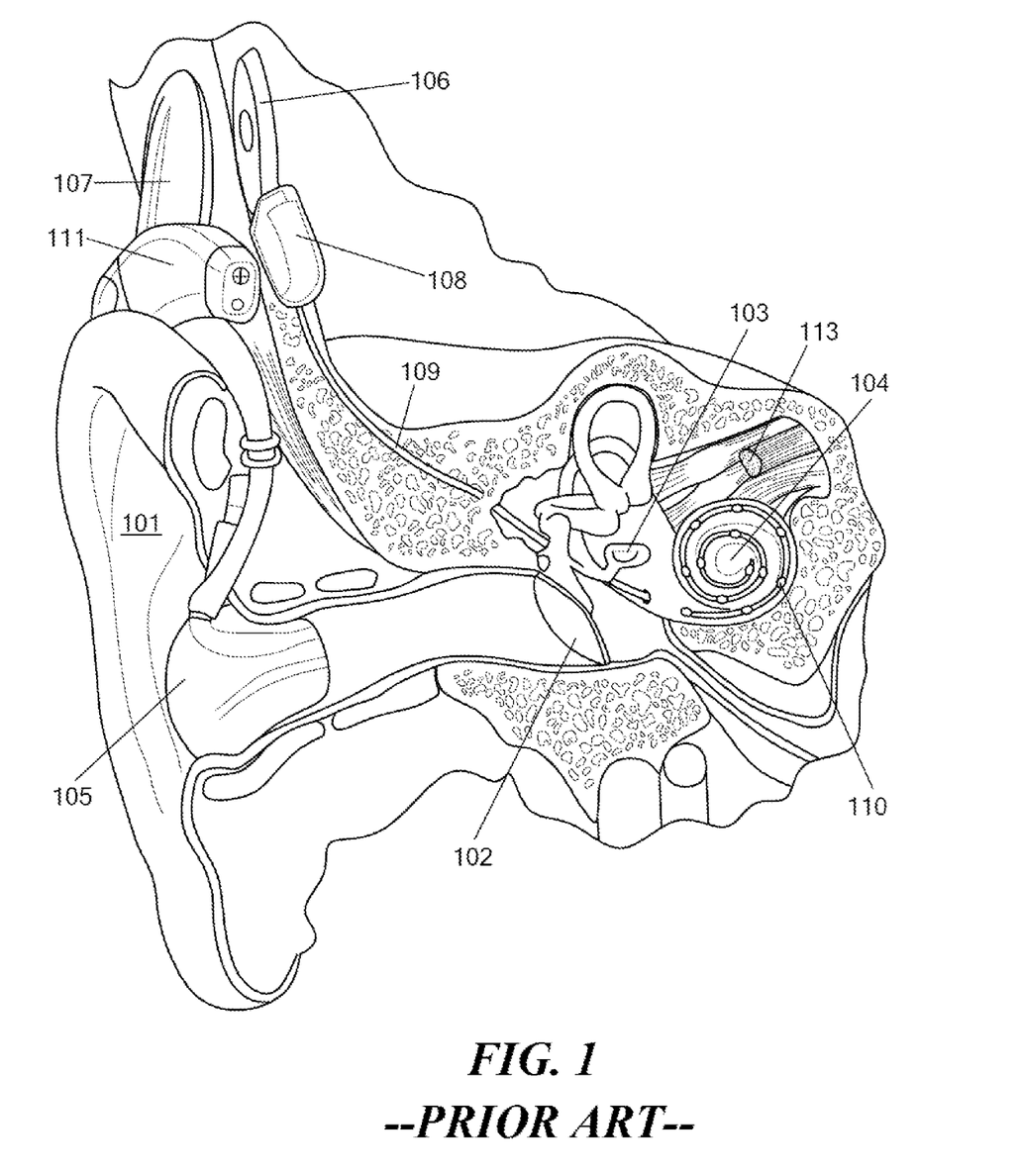
FIG. 1 (prior art) shows a typical human ear having an acoustic electric hearing implant system.

A normal ear transmits sounds as shown in FIG. 1 through the outer ear 101 to the tympanic membrane 102 which moves the bones of the middle ear 103 (malleus, incus, and stapes) that vibrate the oval window and round window membrane openings of the cochlea 104. The cochlea 104 is a long narrow duct wound spirally about its axis for approximately two and a half turns in a human cochlea. It includes an upper channel known as the scala vestibuli and a lower channel known as the scala tympani, which are connected by the cochlear duct. The axial center of the cochlea 104 is called the modiolar where the spiral ganglion cells of the acoustic nerve 113 reside. In response to received sounds transmitted by the middle ear 103, the fluid-filled cochlea 104 functions as a transducer to generate electric pulses which are sensed by the acoustic nerve 113 and sent to the brain.

Hearing is impaired when there are problems in the ability to transduce external sounds into meaningful action potentials along the neural substrate of the cochlea. To improve impaired hearing, hearing prostheses have been developed. For example, when the impairment is related to operation of the middle ear, a conventional hearing aid may be used to provide acoustic-mechanical stimulation to the auditory system in the form of amplified sound to the tympanic membrane. Or when the hearing impairment is associated with the cochlea, a cochlear implant with an implanted electrode carrier can electrically stimulate adjacent auditory neural tissue with small currents.

In some patients with some residual hearing in the lower acoustic frequencies, a conventional hearing aid and a cochlear implant can be combined together in a hybrid Electric Acoustic Stimulation (EAS) system. The hearing aid acoustically amplifies lower acoustic frequencies perceived by human ear, while the cochlear implant electrically stimulates the middle and high frequencies. See von Ilberg et al, *Electric-Acoustic Stimulation of the Auditory System*, ORL 61:334-340; Skarzynski et al, *Preservation of Low Frequency Hearing in Partial Deafness Cochlear Implantation (PDCI) Using the Round Window Surgical Approach*, Acta OtoLaryngol 2007; 127:41-48; Gantz & Turner, *Combining Acoustic and Electrical Speech Processing: Iowa/Nucleus Hybrid Implant*, Acta Otolaryngol 2004; 124:344-347; Gstöttner et al., *Hearing Preservation in Cochlear Implantation for Electric Acoustic Stimulation*, Acta Otolaryngol 2004; 124:348-352; all incorporated herein by reference.

FIG. 1 also shows some components of a typical EAS system which includes an external microphone that provides an acoustic signal input to an external signal processor 111 where two different signal processing paths are developed. An upper acoustic frequency range communications signal containing middle and high frequency range acoustic is converted into a digital data format, such as a sequence of data frames, for transmission via a transmitter coil 107 over a corresponding implanted receiver coil 106 into the electric implant 108. Besides receiving the processed acoustic information, the electric implant 108 also performs additional signal processing such as error correction, pulse formation, etc., and produces an electric stimulation pattern (based on the extracted acoustic information) that is sent through an electrode lead 109 to an implanted electrode array 110. Typically, this electrode array 110 includes multiple electrode contacts on its outer surface that provide selective electric stimulation of the cochlea 104. The external signal processor 111 also creates a lower acoustic frequency range communications signal to a conventional hearing aid 105 in the ear canal which acoustically stimulates the tympanic membrane 102, and in turn the middle ear 103 and cochlea 104.

To achieve optimal hearing preservation outcomes in a large population of EAS patients, a controlled electrode insertion depth was used (e.g., 18-22 mm in order to reach 360 degree of electrode insertion). More particularly, by investigating optimal electrodes, surtical approaches and how deep the electrode can be inserted in order to minimize electrode insertion trauma, higher hearing preservation rates have been achieved. The ultimate goal is the maximum possible electrode insertion depth while preserving acoustic hearing in as broad population of cochlear implantees as possible.

Following surgical implantation, the hearing aid and/or cochlear implant of the EAS subject must be custom fit to optimize its operation with the specific patient user. For the fitting process, it is important, for example, to know if an audible percept is elicited and how loud the percept is. Normally this information is gained using behavioral measures. For example, for each electrode contact the CI user may be asked at what stimulation level the first audible percept is perceived (hearing threshold (THR)) and at what stimulation level the percept is too loud (maximum comfort level (MCL)).

It is of high importance to develop a fitting algorithm for EAS subjects. The individual fitting techniques for the hearing aid and the speech processor of a cochlear implant for electrical stimulation is well described in numerous papers and patents. However, having the combination of both systems on the implanted side, a simple combination of both fitting techniques is not easily achieved. Studies show that separate fittings for the acoustic and electrical stimulations does not lead to an optimized benefit for EAS subjects (See Polak M., Lorens A., Helbig S., McDonald S., McDonald S., Vermeire K., *Fitting of the Hearing System Affects Partial Deafness Cochlear Implant Performance*, Cochlear Implants International, Vol. 11 Supplement 1, June, 2010, 117-21; and Nopp P. and Polak M., *From Electric Acoustic Stimulation to Improved Sound Coding in Cochlear Implants*, Van de Heyning P., Kleine Punte A. (eds), Cochlear Implants and Hearing Preservation. Adv Otorhinolaryngol, Basel, Karger, 2010, Vol. 67:88-95, each of which is hereby incorporated herein by reference). Polak et al. (2010) shows that a single parameter change (e.g., lower frequency end of electrical stimulation, AGC compression, AGC threshold, and lower cut slope) may have a dramatic effect on the benefit of EAS patients for hearing in quiet and/or noisy environments.

Acoustic and electric optimized fitting parameters depend on the level of hearing preserved and preoperative residual hearing. Consequently, it is disadvantageous that the hearing aid component and CI component of the combined audio processor be fitted separately.

SUMMARY OF THE EMBODIMENTS

In accordance with an embodiment of the invention there is provided a method of fitting an Electric Acoustic Stimulation (EAS) system of a patient that has binaural hearing. The patient has an ipsilateral ear and a contralateral ear opposite the ipsilateral ear, with the EAS system associated with the ipsilateral ear of the patient. The method includes developing stimulation parameters of the EAS system unilaterally while taking into account hearing abilities of the contralateral ear. The EAS system is configured based on the developed stimulation parameters.

In accordance with related embodiments of the invention, developing stimulation parameters of the EAS system may include determining frequency coverage for acoustical and/or electrical regions of the EAS system. The method may include determining a frequency range covered by acoustical residual hearing associated with the EAS system, and determining a frequency range covered by electrical stimulation associated with the EAS system. If there is a frequency gap that is not covered by either the acoustical residual hearing or the electrical stimulation of the EAS system, the method may further include developing stimulation parameters such that the frequency gap is covered by electrical stimulation. If there is overlap in frequency coverage of the acoustical residual hearing and the electrical stimulation of the EAS system, the method may further include developing stimulation parameters to decrease electrical stimulation by at least one apical electrode of the EAS system, so as to allow only acoustical stimulation in the region of usable acoustical hearing.

In accordance with further related embodiments of the invention, developing stimulation parameters of the EAS system unilaterally may include maintaining functional binaural sound processing of the patient. This may include optimizing interaural level differences (ILD) and/or optimizing interaural time delays (ITD).

In still further related embodiments of the invention, the method may include determining treatment of the contralateral ear. The treatment of the contralateral ear may involve a hearing aid, natural hearing, an EAS system, and/or a cochlear implant.

In accordance with another embodiment of the invention, a system for modifying stimulation parameters of an Electric Acoustic Stimulation (EAS) system of a patient that has binaural hearing is provided. The patient has an ipsilateral ear and a contralateral ear opposite the ipsilateral ear, with the EAS system associated with the ipsilateral ear of the patient. The system includes a controller configured to communicate with the EAS system, and to develop and set stimulation parameters of the EAS system unilaterally while taking into account hearing abilities on the contralateral side of the patient.

In accordance with related embodiments of the invention, the stimulation parameters may pertain to acoustical and/or electrical coverage of the EAS system. The controller may be further configured to determine a frequency range covered by acoustical residual hearing associated with the EAS system, and to determine a frequency range covered by electrical stimulation associated with the EAS system. If there is a frequency gap that is not covered by either the acoustical residual hearing or the electrical stimulation of the EAS system, the controller may be configured to develop stimulation parameters of the EAS system such that the frequency gap is covered by electrical stimulation. If there is overlap in frequency coverage of the acoustical residual hearing and the electrical stimulation of the EAS system, the controller may be configured to develop stimulation parameters of the EAS system so as to decrease electrical stimulation of at least one apical electrode of the EAS system, thereby allowing only acoustical stimulation in the region of usable acoustical hearing.

In accordance with related embodiments of the invention, the controller may be configured to develop stimulation parameters of the EAS system unilaterally so as to maintain functional binaural sound processing of the patient. The controller may be configured to develop stimulation parameters of the EAS system unilaterally so as to optimize interaural level differences (ILD and/or interaural time delays (ITD).

In accordance with further related embodiments of the invention, the controller may be configured to determine treatment of the contralateral ear. Such treatment may include a hearing aid, an EAS system, and/or a cochlear implant associated with the contralateral ear, wherein the controller may be configured to communicate with the hearing aid, the EAS system, and/or the cochlear implant.

In accordance with another embodiment of the invention, a system for modifying stimulation parameters of an Electric Acoustic Stimulation (EAS) system of a patient that has binaural hearing is provided. The patient has an ipsilateral ear and a contralateral ear opposite the ipsilateral ear, the EAS system associated with the ipsilateral ear of the patient. The system includes means for developing parameters of the EAS system unilaterally while taking into account hearing abilities of the contralateral ear, and means for configuring the EAS system with the developed stimulation parameters.

In accordance with related embodiments of the invention, the means for developing stimulation parameters of the EAS system may include means for determining coverage for acoustical and/or electrical regions of the EAS system. Determining coverage may include means for determining a frequency range covered by acoustical residual hearing associated with the EAS system, and means for determining a frequency range covered by electrical stimulation associated with the EAS system. If there is a frequency gap that is not covered by either the acoustical residual hearing or the electrical stimulation of the EAS system, the means for developing the stimulation parameters may include covering the frequency gap with electrical stimulation. If there is overlap in frequency coverage of the acoustical residual hearing and the electrical stimulation of the EAS system, the means for developing the stimulation parameters may include decreasing electrical stimulation of at least one apical electrode of the EAS system so as to allow only acoustical stimulation in the region of usable acoustical hearing.

In accordance with further related embodiments of the invention, the means for developing stimulation parameters of the EAS system unilaterally may include means for maintaining functional binaural sound processing of the patient. The means for developing stimulation parameters of the EAS system unilaterally may include means for optimizing interaural level differences (ILD) and/or interaural time delays (ITD).

In accordance with still further related embodiments of the invention, the system may include means for determining treatment of the contralateral ear. Such treatment may involve a hearing aid, natural hearing, an EAS system, and/or a cochlear implant.

In accordance with another embodiment of the invention, a computer program product encoded in a non-transitory computer-readable medium for fitting an Electric Acoustic Stimulation (EAS) system of a patient that has binaural hearing is provided. The patient has an ipsilateral ear and a contralateral ear opposite the ipsilateral ear, the EAS system associated with the ipsilateral ear of the patient. The product includes program code for developing stimulation parameters of the EAS system unilaterally while taking into account hearing abilities of the contralateral ear, and program code for configuring the EAS system based on the developed stimulation parameters.

In accordance with related embodiments of the invention, the program code for developing stimulation parameters of the EAS system may include program code for determining frequency coverage for acoustical and/or electrical regions of the EAS system. The product may include program code for determining whether there is a frequency gap that is not covered by either the acoustical residual hearing or the electrical stimulation of the EAS system, and if so, developing stimulation parameters such that the frequency gap is covered by electrical stimulation. The product may include program code for determining whether there is overlap in frequency coverage of the acoustical residual hearing and the electrical stimulation of the EAS system, and if so, developing stimulation parameters to decrease electrical stimulation by at least one apical electrode of the EAS system, so as to allow only acoustical stimulation in the region of usable acoustical hearing.

In accordance with further related embodiments of the invention, the program code for developing stimulation parameters of the EAS system unilaterally may include program code for maintaining functional binaural sound processing of the patient. For example, the product may include program code for optimizing interaural level differences (ILD) and/or interaural time delays (ITD).

In accordance with still further embodiments of the invention, the product may include program code for determining treatment of the contralateral ear. Such treatment may include hearing aid, natural hearing, an EAS system, and/or a cochlear implant.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments of the invention, an optimized Electric Acoustic Stimulation (EAS) System fitting takes into account hearing abilities of the contralateral ear to obtain equal bilateral acoustic and/or electric performance. In further embodiments, electric and acoustic hearing components of the EAS system are fitted in a coordinated manner. Details are described below.

Figure 2:
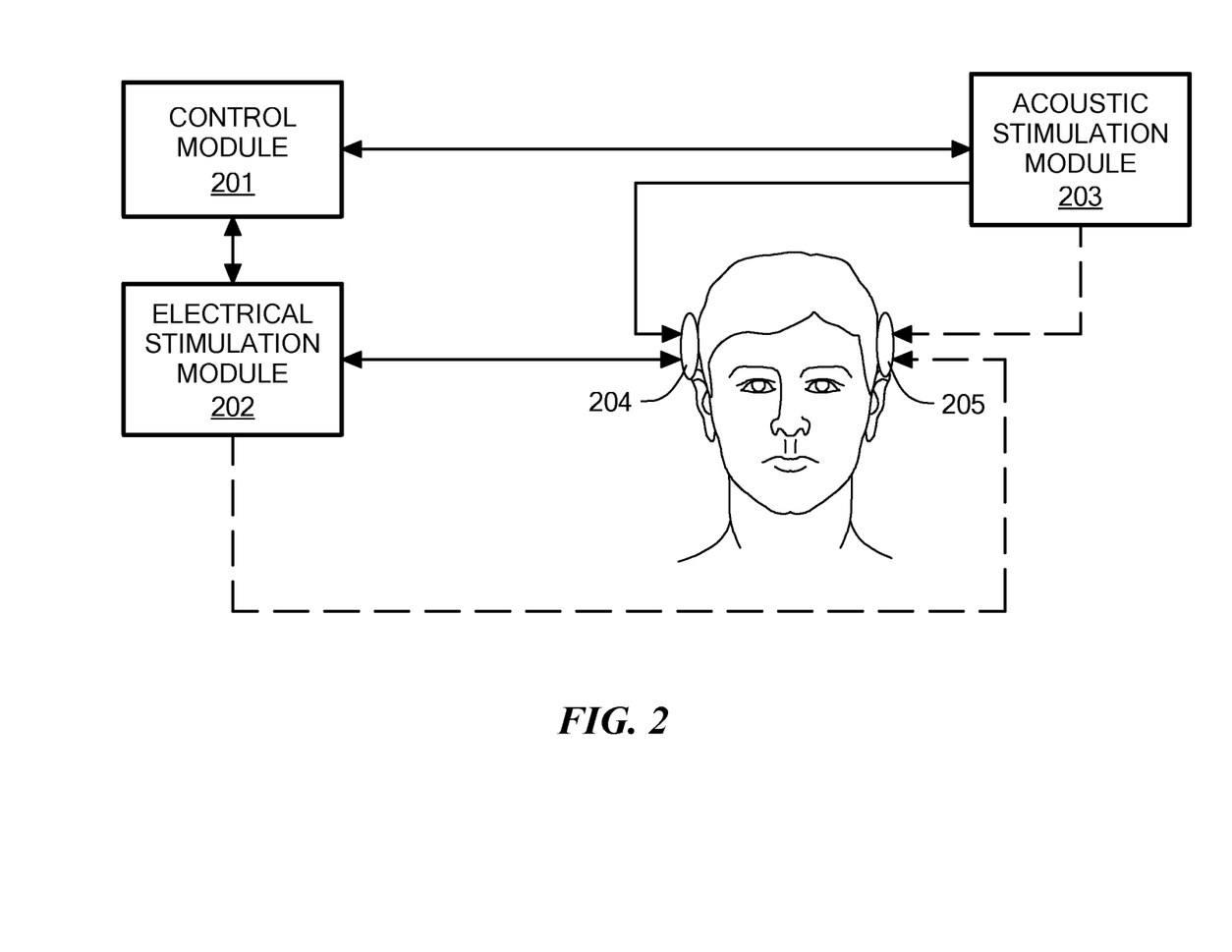
FIG. 2 shows various functional blocks in a system for patient fitting of a hybrid acoustic-electrical hearing implant system, in accordance with an embodiment of the present invention.

FIG. 2 shows various functional blocks in a system for patient fitting of a hybrid Electric Acoustic (EAS) hearing implant system, in accordance with an embodiment of the present invention. The patient has an ipsilateral ear and a contralateral ear opposite the ipsilateral ear, with the EAS system 204 associated with the ipsilateral ear of the patient. The EAS system includes one or more audio signal processors, that may be external and/or implanted, that process an acoustic signal input so as to ultimately control acoustic amplification and/or electrical stimulation signals provided by the hearing aid and cochlear implant, respectively.

Control module 201 contains a combination of software and hardware for controlling the stimulation of electrical and acoustical pulses. For example, control module 201 may be based on a Maestro system manufactured by Med-E1, Innsbruck, Austria. The electrical stimulation pulses are transmitted from the electrical stimulation module 202 (e.g., including a Device Interface Box (DIB)) to the audio prosthesis 204 which delivers them via the cochlear implant electrodes to the target nerve tissue. The control module 201 may also include software for recording near field responses from the cochlear implant electrodes. An acoustic stimulation module 203 (e.g., including a HI-PRO Box programming interface) delivers acoustic stimuli to the audio prosthesis 204 for delivery via the ear canal to the middle ear. For example, the acoustic stimulation module 203 may be an HI-PRO Box programming interface from Noah Inc. The control module may also include software and hardware for controlling the stimulation of electrical and acoustical pulses, and/or recording of responses, via, without limitation, the electrical stimulation module 202 and/or acoustic stimulation module 203, at the contralateral ear, which may or may not include a hearing aid or implant 205. Based on the measurements taken by the fitting system, fitting parameters of the audio processor associated with the EAS system of at least the ipsilateral ear are determined and set.

Figure 3:
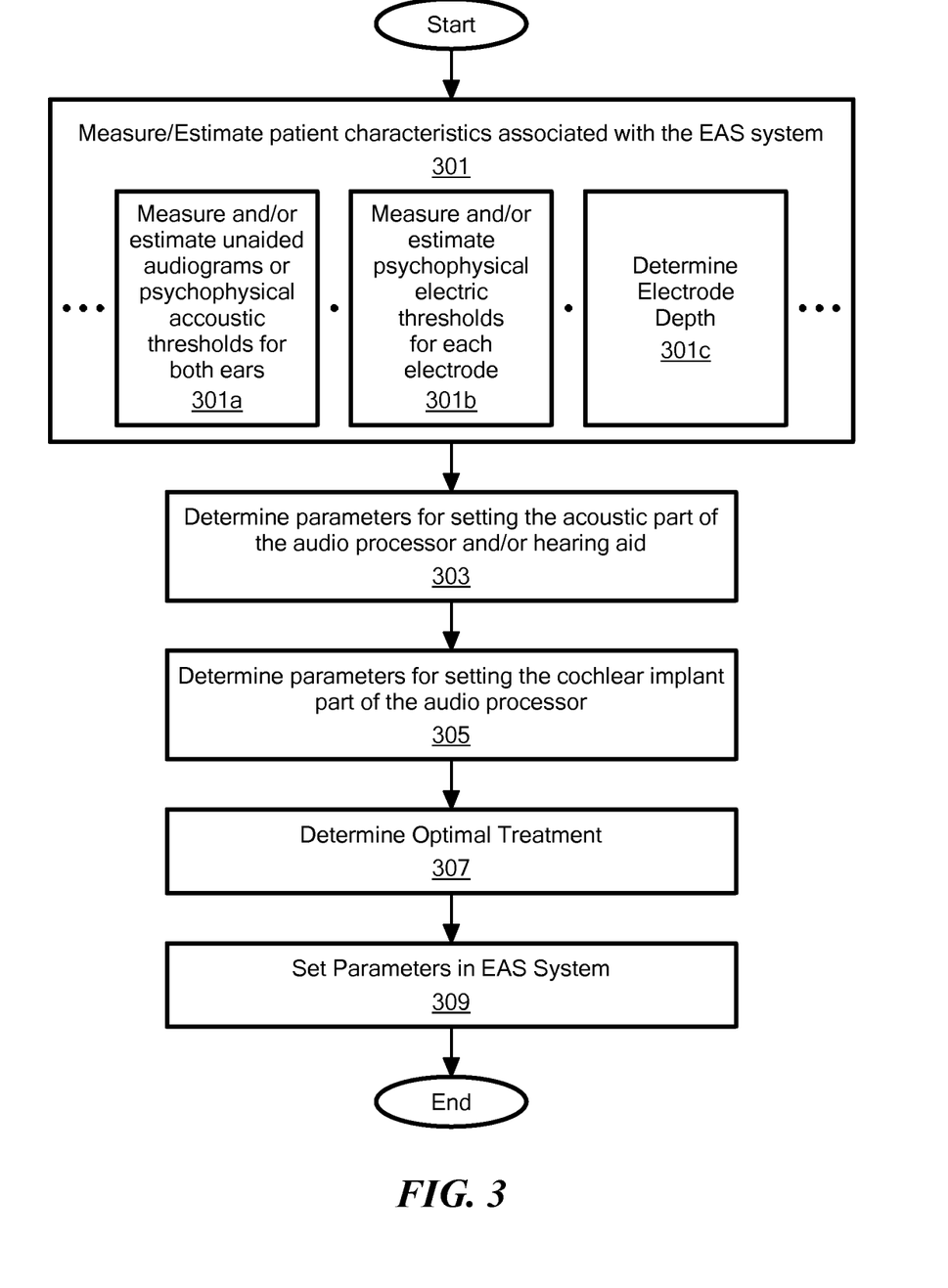
FIG. 3 shows various logical steps that may be performed in fitting an EAS system, in accordance with an embodiment of the invention.

FIG. 3 shows various logical steps that may be performed in fitting an EAS system, in accordance with an embodiment of the invention. As described above, the EAS system includes both electrical stimulation via, for example, a cochlear implant, while preserving some level of natural or amplified (e.g., via a hearing aid) acoustic hearing.

The fitting advantageously may make use of contralateral non-implanted ear properties to fit the ipsilateral ear (implanted side) audio processor (referred herein as condition 1). The fitting may utilize, for example, binaural properties, such as interaural time difference (ITD) and/or and interaural level difference (ILD)) for both the ipsilateral and contralateral ear. The fitting may measure and/or determine appropriate overlap between acoustically amplified and electrically stimulated range (referred herein as condition 2). The fitting may coordinate acoustic and electric fitting parameters of the audio processor of the EAS system (referred herein as condition 3).

To begin with, various patient characteristics associated with the EAS system may be measured and/or estimated, step 301. For example, unaided audiograms for both ears may be measured and/or estimated, and/or psychophysical acoustic thresholds determined, step 301a. Additionally, various psychophysical electric thresholds (for example, most comfortable levels (MCLs) and/or threshold levels) for each electrode for the implanted ear may be measured and/or estimated, step 301b. Furthermore, after placement of the electrodes into the cochlea, an electrode insertion depth may be determined, step 301c. Electrode insertion depth may be determined, without limitation, by a postoperative CT scan. Using the Greenwood frequency scale, the determined depth may be used, without limititation, to calculate the electrical frequency coverage. For example, the insertion depth of an EAS electrode is typically controlled to a relatively shallow depth in the scala tympani which typically achieves about 360° of electrode insertion, around 18-22 mm. According to the Greenwood scale, 360° of electrode insertion in the tonotopically organized cochlea covers the acoustic frequency region from 1 kHz and higher. See Greenwood, A Cochlear *Frequency-Position Function For Several Species—29 Years Later*, J Acoustic Soc Am, 1990; 87(6):2592-2605; incorporated herein by reference. Note that where the residual acoustic hearing frequencies are lower than 1 kHz, a frequency gap arises between the highest frequency covered by residual acoustic-based hearing and the lowest frequency covered by the electrical implant. Furthermore, where the residual acoustic hearing frequencies are higher than 1 kHz, frequency overlap arises between the highest frequency covered by residual acoustic-based hearing and the lowest frequency covered by the electrical implant. It is to be understood that the various measurements and/or estimations performed in step 301 can be performed in any order.

Based on the above-described measurements and/or estimates of the patient characteristics, and under consideration of conditions 1-3, parameters for setting the acoustic part of the audio processor and/or hearing aid are determined, step 303. These parameters may include, without limitation, number of acoustic channels, gain, channel compression, compression knee point, frequency range for acoustic amplification, and/or processing of acoustic delay, discussed in more detail below.

Additionally, based on the above-described measurements and/or estimates of the patient characteristics, and under consideration of conditions 1-3, parameters for setting the cochlear implant part of the audio processor are determined, step 305. These parameters may include, without limitation, lower frequency end, number of deactivated most apical channels, processing of electric delay, front end compression, and/or compression knee point, discussed in more detail below.

The most optimal treatment for the implanted EAS patient may also be determined based on the above-described measurements and/or estimates of the patient characteristics, step 307. These treatments include, without limitation, in addition to the EAS system on the ipsilateral ear, the following treatments associated with the contralateral ear: a contralateral hearing aid, a contralateral EAS system, or contralateral natural hearing.

Obtaining contralateral hearing thresholds may be performed for the purposes of setting EAS parameters of the ipsilateral ear, and that of any hearing aid/implant of the contralateral ear, such that equal loudness is obtained for both ears. This may advantageously improve localization and speech performance in real-live environments, and in particular, noisy environments.

In illustrative embodiments of the invention, the above-described methodology maintains functional binaural sound processing (allowing for processing of interaural time difference (ITD) and interaural level difference (ILD) processing) for both ears, thus allowing for the better use of binaural cues. This may include controlled loudness perception in a wide dynamic range and time delay in both ears. In general, better precision may be achieved by obtaining complex information about the hearing. This may include measurement of first hearing threshold, most comfortable levels (MCL) and uncomfortable levels for each executive audiological frequency.

Once the optimal operating parameters for the ipsilateral EAS system are determined, they are provided to and set in the EAS system, step 309. If the contralateral side also includes a device such as a hearing aid, cochlear implant or EAS system, these devices may also be fitted with any determined parameters. In various embodiments, the contralateral side may utilize either natural hearing or hearing amplification, and may not require an implant. Alternatively, the above-described methodology may be used in a bilateral EAS fitting. In such cases, the measurement or estimation of psychophysical electric thresholds (for example, MCLs and/or Thresholds) may be performed for both ears. The above-described methodology may ensure that both cochlear implants elicit approximately equal loudness and time delay for the entire electric frequency range.

Electric and acoustic fitting parameters of an EAS system differ from those when only a hearing aid or cochlear implant is used. In order to optimize the benefit to the patient, both the hearing aid and the cochlear implant both HA and CI should be programmed in a controlled manner, as described above. A discussion of these parameters is described below in more detail.

Fitting parameters for the acoustic part of the audio processor or hearing aid may include the following.

a. the number of acoustic channels
b. gain—Treatment for summation effect of electrical and acoustic hearing may be performed. Optimization may include achieving equal loudness on both ears, as described above, channel dependent.
c. loudness compression of the acoustic part—Generally, loudness compression includes static parameters of automatic gain control (AGC) including, without limitation, expansion threshold, linear gain region, and compression threshold. Optimization may include achieving equal loudness on both ears. In case a patient uses a contralateral hearing aid or cochlear implant for the selected frequency range, the frequency specific loudness should be equal. Compression may be dependent on the level of ipsilateral and contralateral hearing for a specific frequency.
d. frequency range for acoustic amplification—Typically, only a small acoustic and electric frequency overlap is beneficial.
e. processing delay of the acoustic part—Both acoustical and electrical hearing should be processed in a controlled manner. The processing delay of the acoustic part is necessary to adjust according to the used frequency range of the acoustic amplification, frequency range of the electric stimulation and delays of the acoustic and electric processing pathway of the audio processor. The delay between the electrical and the acoustic processing may be controlled ipsilateral and/or contralateral.

Fitting parameters for the electrical stimulation part of the audio processor (e.g., speech processor of a cochlear implant) may include the following.
a. lower frequency end—Only small acoustic and electric frequency overlap is beneficial. In general, the lower frequency end may be obtained from the unaided audiogram at the level of 65 dBHL (subjects with sky sloped audiograms). For subjects with flatter audiograms, the lower frequency end may be obtained from the unaided audiogram at the level when hearing is non-functional (may vary up to 80-90 dBHL).
b. number of deactivated most apical channels
c. volume—Treatment for summation effect of Electrical and Acoustic hearing may advantageously be performed.
d. processing delay
e. front-end compression—in case a patient uses contralateral hearing aid or cochlear implant for the selected frequency range, the frequency specific loudness should be equal.

Setting of the AGC static parameters and acoustic gain will now be described in more detail. The static parameters of AGC may include, without limitation, expansion threshold, linear gain region, compression threshold and gain. Based on unaided audiograms, the values for these static parameters may be determined.

The static AGC parameters may be defined based on the hearing loss for each specific audiometric frequency or respective channel for both ears. For example, for 30 dB Hearing Loss, the compression rate may be 1:1, with the compression rate linearly increasing with the hearing loss. Illustratively, the compression rate for 80 dB HL may be 1:2.

Especially in a case when the contralateral ear does not have any functional residual hearing and the patient is not implanted with any cochlear implant, a number of compression formulas may be provided to a patient, from which the patient may then choose (e.g., 3 different compression formulas: low (up to 1:1.5), medium (up to 1:2) and high compression (up to 1:3). Compression threshold may increase linearly from a certain hearing loss level. For example, from 70 dB Hearing Loss the compression threshold may increase from, without limitation, 50 dB to 70 dB up to the level of hearing loss of 95 dB Hearing Loss.

The determination of gain may be closely related to the chosen formulas for the compression. For each compression formula, a different formula for gain may be utilized, and in general, the gain may linearly increase with the increasing hearing loss for a particular channel.

For example, a lower gain may be associated with the low compression formula. Illustratively, for 20 dB Hearing Loss, the gain may be 0 dB, and for 80 dB Hearing Loss, the gain may be 40 dB. For the high compression formula, the gain may be set higher. For example, for 20 dB Hearing Loss, the gain may be 0 dB, and for 80 dB Hearing Loss, the gain may be 50 dB.

Generally, if residual hearing is poor (approximately 80-90 dB Hearing Loss), the acoustic gain may be set to high values (for example, a gain up to 50-60 dB). Alternatively, if residual hearing is relatively good (approximately 30-20 dB Hearing Loss), the acoustic gain may be set to low values. In the event hearing is normal or near to normal (approximately 0 up to 20-30 dB) for a certain channel, no amplification may be performed.

In case of usable but impaired contralateral low frequency hearing, both ears may be adjusted with acoustic amplification. Especially in cases when both ears clearly differ in the amount of usable hearing and both ears use different hearing aids, the testing of equal loudness between both ears may be of particular complexity/concern. In such cases, the same hearing aids or hearing aids with similar processing algorithm may be utilized so as to maintain equal parameters. This may include amount of gain, number of amplified channels, specific aided audiogram and/or acoustic delay.

In various embodiments, the acoustically poorer ear should be amplified in order to match the better ear (i.e., the contralateral non-implanted ear). The equal loudness should be achieved as equally as possible for as wide dynamic range as possible, especially in the speech perception area or area with the highest sensitivity (approximately 50-80 dB Hearing Loss). If equal hearing aids or hearing aids with similar processing algorithms are utilized, the loudness may be easily equalized for a wide dynamic range, for example, 20 to 120 dB SPL. In case of normal or near-to-normal low frequency hearing, no acoustical amplification setting may be necessary.

Figure 4A:
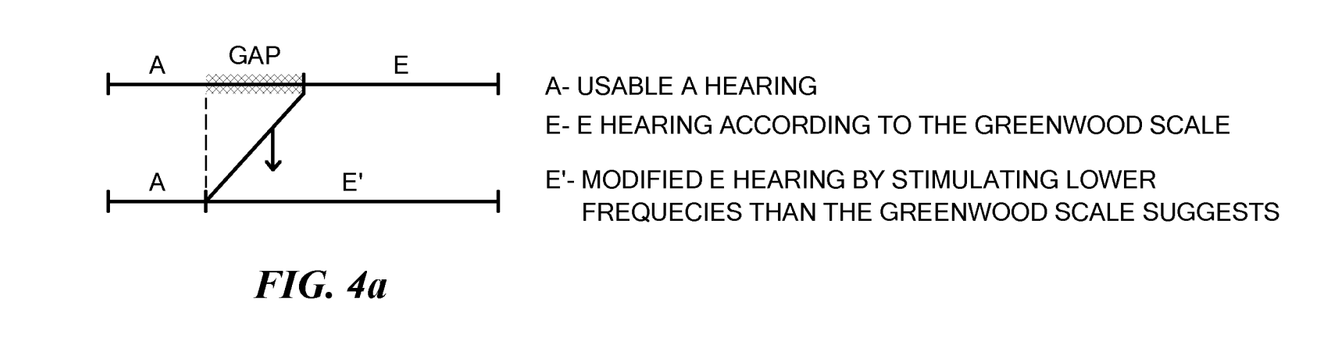
FIG. 4a shows a gap between the usable acoustic residual hearing and frequency range covered by the electrode insertion according to the Greenwood scale treated by electrical stimulation, in accordance with an embodiment of the invention.
Figure 4B:
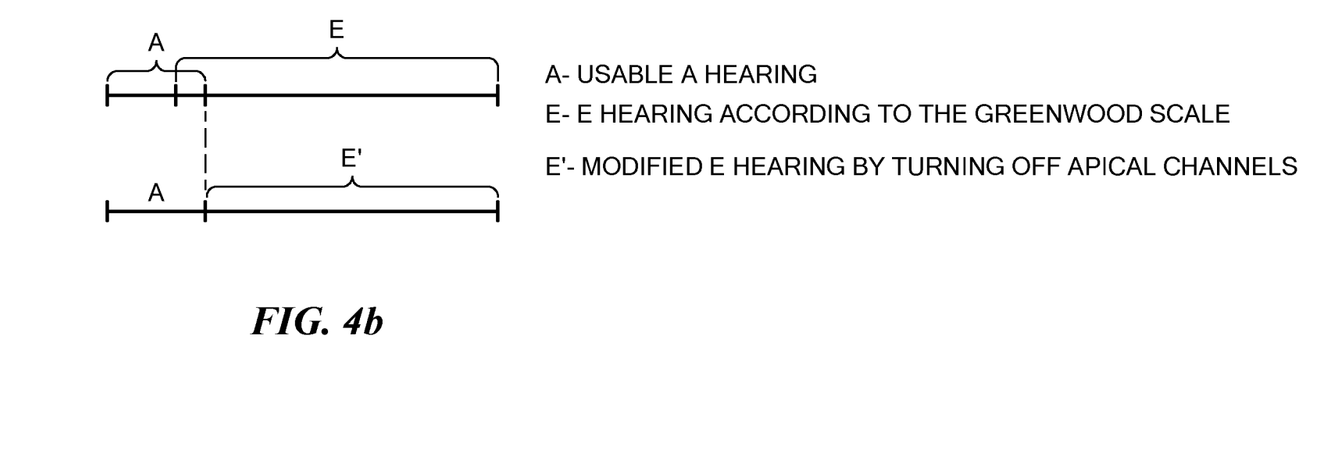
FIG. 4b shows overlap between the usable acoustic residual hearing and frequency range covered by the electrode insertion according to the Greenwood scale treating by turning off the most apical electrodes in order to allow acoustic stimulation in the region of usable acoustic hearing, in accordance with an embodiment of the invention.

Upon measuring the usable acoustic hearing and electrode insertion depth (which, as described above, may be then further used to calculate the frequency range covered by electrical stimulation), a frequency gap or alternatively, a frequency overlap, between acoustic hearing and electrical stimulation for a given patient may be determined. Any remaining gap between the usable acoustic residual hearing and frequency range covered by the electrode insertion according to the Greenwood scale may be treated by electrical stimulation, as shown in FIG. 4a, in accordance with an embodiment of the invention. In case of overlap between the usable acoustic residual hearing and frequency range covered by the electrode insertion according to the Greenwood scale, the most apical electrodes can be turned off in order to allow acoustic stimulation in the region of usable acoustic hearing, as shown in FIG. 4b, in accordance with an embodiment of the invention. Again, electrical stimulation is used in the region with no useable acoustic hearing.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

For example, a pseudo code representation of a generic embodiment might be set forth as follows:

| Process PatientFitting |
|---|
| measure and/or estimate patient characteristics associated with the EAS system, including both ipsilateral and contralateral ear |
| determine parameters for setting the acoustic part of the audio processor and/or hearing aid |
| determine parameters for setting the cochlear implant part of the audio processor |
| set operating parameters of the EAS system |

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of fitting an Electric Acoustic Stimulation (EAS) system of a patient that has binaural hearing, the patient having an ipsilateral ear and a contralateral ear opposite the ipsilateral ear, the EAS system configured to be used on the ipsilateral ear of the patient whose contralateral ear is not associated with a hearing device, the method comprising:
   obtaining an unaided audiogram of the contralateral ear;
   determining hearing thresholds of the contralateral ear based on the unaided audiogram;
   developing stimulation parameters of the EAS system unilaterally to obtain equal loudness for both ears based, at least in part, on the hearing thresholds of the contralateral ear; and
   configuring the EAS system based on the developed stimulation parameters.

2. The method according to claim 1, wherein developing stimulation parameters of the EAS system includes developing stimulation parameters pertaining to acoustical and/or electrical coverage of the EAS system.

3. The method according to claim 2, further comprising:
   determining a frequency range covered by acoustical residual hearing in the ipsilateral ear that is associated with the EAS system; and
   determining a frequency range covered by electrical stimulation associated with the EAS system.

4. The method according to claim 3, wherein if there is a frequency gap that is not covered by either the acoustical residual hearing or the electrical stimulation of the EAS system, the method further includes developing stimulation parameters such that the frequency gap is covered by electrical stimulation.

5. The method according to claim 3, wherein if there is overlap in frequency coverage of the acoustical residual hearing and the electrical stimulation of the EAS system, the method further includes developing stimulation parameters to decrease electrical stimulation by at least one apical electrode of the EAS system, so as to allow only acoustical stimulation in regions of acoustical residual hearing.

6. The method according to claim 1, wherein developing stimulation parameters of the EAS system unilaterally includes providing binaural sound processing of the patient.

7. The method according to claim 6, wherein providing binaural sound processing of the patient includes optimizing interaural level differences (ILD).

8. The method according to claim 6, wherein providing binaural sound processing of the patient includes optimizing interaural time delays (ITD).

9. A system for modifying stimulation parameters of an Electric Acoustic Stimulation (EAS) system of a patient that has binaural hearing, the patient having an ipsilateral ear and a contralateral ear opposite the ipsilateral ear, the EAS system configured to be used on the ipsilateral ear of the patient whose contralateral ear is not associated with a hearing device, the system comprising:
   a controller configured to communicate with the EAS system, the controller further configured to:
      determine hearing thresholds of the contralateral ear based on an unaided audiogram of the contralateral ear;
      develop and set stimulation parameters of the EAS system unilaterally to obtain equal loudness for both ears based, at least in part, on the hearing thresholds of the contralateral ear.

10. The system according to claim 9, wherein the stimulation parameters include stimulation parameters pertaining to acoustical and/or electrical coverage of the EAS system.

11. The system according to claim 10, where the controller is further configured to:
   determine a frequency range covered by acoustical residual hearing in the ipsilateral ear that is associated with the EAS system; and
   determine a frequency range covered by electrical stimulation associated with the EAS system.

12. The system according to claim 11, wherein if there is a frequency gap that is not covered by either the acoustical residual hearing or the electrical stimulation of the EAS system, the controller is configured to develop stimulation parameters of the EAS system such that the frequency gap is covered by electrical stimulation.

13. The system according to claim 11, wherein if there is overlap in frequency coverage of the acoustical residual hearing and the electrical stimulation of the EAS system, the controller is configured to develop stimulation parameters of the EAS system so as to decrease electrical stimulation of at least one apical electrode of the EAS system, thereby allowing only acoustical stimulation in regions of acoustical residual hearing.

14. The system according to claim 9, wherein the controller is configured to develop stimulation parameters of the EAS system unilaterally so as to provide binaural sound processing of the patient.

15. The system according to claim 14, wherein the controller is configured to develop stimulation parameters of the EAS system unilaterally so as to optimize interaural level differences (ILD).

16. The system according to claim 14, wherein the controller is configured to develop stimulation parameters of the EAS system unilaterally so as to optimize interaural time delays (ITD).

* * * * *